(12) United States Patent
Borg et al.

(10) Patent No.: US 10,823,677 B2
(45) Date of Patent: Nov. 3, 2020

(54) CONCENTRATION ASSAY

(75) Inventors: Peter Borg, Uppsala (SE); Asa Frostell-Karlsson, Uppsala (SE); Markku Hamalainen, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 877 days.

(21) Appl. No.: 12/994,297

(22) PCT Filed: Jun. 1, 2009

(86) PCT No.: PCT/SE2009/050638
§ 371 (c)(1),
(2), (4) Date: Nov. 23, 2010

(87) PCT Pub. No.: WO2009/148396
PCT Pub. Date: Dec. 10, 2009

(65) Prior Publication Data
US 2011/0076703 A1 Mar. 31, 2011

(30) Foreign Application Priority Data

Jun. 2, 2008 (SE) ..................................... 0801304
Apr. 24, 2009 (SE) ..................................... 0950272

(51) Int. Cl.
*G01N 21/65* (2006.01)
*G01N 21/552* (2014.01)
*G01N 33/543* (2006.01)

(52) U.S. Cl.
CPC ......... *G01N 21/658* (2013.01); *G01N 21/553* (2013.01); *G01N 33/54306* (2013.01); *G01N 33/54373* (2013.01)

(58) Field of Classification Search
CPC ............... G01N 21/658; G01N 21/553; G01N 33/54306; G01N 33/54373
See application file for complete search history.

(56) References Cited

U.S. PATENT DOCUMENTS

| | | | |
|---|---|---|---|
| 5,242,828 A | 9/1993 | Bergstrom et al. | |
| 5,313,264 A | 5/1994 | Ivarsson et al. | |
| 5,436,161 A | 7/1995 | Bergstrom et al. | |
| 5,492,840 A | 2/1996 | Malmqvist et al. | |
| 5,795,791 A * | 8/1998 | Hirai et al. | 436/501 |
| 6,477,392 B1 * | 11/2002 | Honigs et al. | 600/316 |
| 2003/0138870 A1 | 7/2003 | Tanaka et al. | 435/7.93 |
| 2006/0094060 A1 | 5/2006 | Jarhede et al. | |
| 2009/0092620 A1 * | 4/2009 | Moste | A61K 31/737 424/147.1 |
| 2011/0070574 A1 * | 3/2011 | Borg et al. | 435/5 |

FOREIGN PATENT DOCUMENTS

| | | |
|---|---|---|
| EP | 0276142 A1 | 7/1988 |
| EP | 0 973 023 | 1/2000 |
| JP | 0354467 A | 3/1991 |
| WO | WO 97/09608 | 3/1997 |
| WO | 9826288 A1 | 6/1998 |
| WO | WO2006/041392 | * 10/2004 ............. G01N 33/53 |
| WO | 2006001749 A1 | 1/2006 |
| WO | WO 2006/041392 | 4/2006 |

OTHER PUBLICATIONS

Okumura et al, Determination of biotinylated proteins as an index for purification of plasma membrane using surface plasmon resonance-based optical biosensor, 2005, Cytotechnology, 47: pp. 50-67.*
Taylor et al., Quantitative detection of tetrodotoxin (TTX) by a surface plasmon resonance (SPR) sensor, 2007, Sensors and Actuators B 130: pp. 120-128.*
Yang et al., Detection of picomolar levels of interleukin-8 in human saliva by SPR, Lab Chip, 2005, 5, 1017-1023.*
GE Healthcare, Biacore Concentration Analysis Handbook, pp. 1-100, 2007, retrieved from http://www.iqm.csic.es/wp-content/uploads/2013/equipamiento/spr/BR-1005-12AB%20Biacore%20Concentration%20Analysis%20Handbook%20(web).pdf on Mar. 23, 2015.*
Motulsky et al., Fitting Models to Biological Data using Linear and Nonlinear Regression, pp. 1-351, 2003, retrieved from http://www.mcb5068.wustl.edu/MCB/Lecturers/Baranski/Articles/RegressionBook.pdf on Mar. 24, 2015.*
Karlsson et al., Biosensor Analysis of Drug-Target Interactions: Direct and Competitive Binding Assays for Investigation of Interactions between Thrombin and Thrombin Inhibitors, Analytical Biochemistry, 278(1), 2000, 1-13.*
Nishimura, Development and evaluation of a direct sandwich-enzyme-linked immunosorbent assay for the quantification of human hepatic triglyceride lipase mass in human plasma, Journal of Immunological Methods 235, 2000, 41-51.*
Okumura, S., et al., Cytotechnology, (2005), 47:59-67.
Amano, Y., et al., Analytical and Bioanalytical Chemistry, 381(1):156-164 (2005).
Dillon, P., et al., Biosensors and Bioelectronics, 18(2-3):217-227 (2003).
Dillon, P., et al., Journal of Immunological Methods, 296(1-2):77-82 (2005).
Vancott, T., et al., Journal of Immunological Methods, 146(2):163-176 (1992).

(Continued)

*Primary Examiner* — Andrea S Grossman
(74) *Attorney, Agent, or Firm* — Hanley, Flight and Zimmerman, LLC (57) ABSTRACT

A method of determining the concentration of at least one analyte in a plurality of samples by sequentially subjecting each sample to an analysis cycle comprises contacting the sample or a sample-derived solution with a sensor surface supporting a species capable of specifically binding the analyte or an analyte-binding species, detecting the amount of binding to the sensor surface, and regenerating the sensor surface to prepare it for the next analytical cycle, and based on the detected binding to the sensor surface determining the concentration of analyte in each sample using virtual calibration data calculated for each analysis cycle from real calibration data obtained by contacting the solid phase with samples containing known concentrations of analyte.

18 Claims, 10 Drawing Sheets

(56) References Cited

OTHER PUBLICATIONS

Yang, L.-M., et al., Analytical Chemistry, 80(4):933-943 (2008).
EP Search Report dated Sep. 14, 2011.
Schofield et al., "Determination of Affinities of a Panel of IgGs and Fabs for Whole Enveloped (Influenza A) Virions using Surface Plasmon Resonance", Journal of Virological Methods, vol. No. 62, Issue No. 1, pp. 33-42, Oct. 1996, 10 pages.
Jiao, "Measuring the Concentration of the Solution by SPR Detection Technique", Huazhong Normal University National Physics Base Class, pp. 98-103, 2004, 13 pages.
Boltovets et al., "Detection of Plant Viruses using a Surface Plasmon Resonance via Complexing with Specific Antibodies", Journal of Virological Methods, vol. No. 121, Issue No. 1, pp. 101-106, Oct. 2004, 6 pages.
Mohler et al. "Mathematical Model of Influenza A Virus Production in Large-Scale Microcarrier Culture", Biotechnology and Bioengineering, vol. No. 90, Issue No. 1, pp. 46-58, Apr. 5, 2005, 13 pages.
Xiu et al., "Detection of Avian Influenza Virus Using an Interferometric Biosensor", Analytical and Bioanalytical Chemistry, vol. No. 389, Issue No. 4, pp. 1193-1199, Aug. 21, 2007, 7 pages.
Chinese Office Action Issued in connection with corresponding CN Application No. 200980121158.1 dated Nov. 2, 2012, 11 pages.
Chinese Office Action Issued in connection with corresponding CN Application No. 200980121159.6 dated Nov. 5, 2012, 11 pages.
Indian Office Action Issued in connection with corresponding IN Application No. 8035/DELNP/2010 dated Jul. 19, 2016, 9 pages.

\* cited by examiner

CONCENTRATION ASSAY

CROSS-REFERENCE TO RELATED APPLICATIONS

This application is a filing under 35 U.S.C. § 371 and claims priority to international patent application number PCT/SE2009/050638 filed Jun. 1, 2009, published on Dec. 10, 2009 as WO 2009/148396, which claims priority to application number 0801304-7 filed in Sweden on Jun. 2, 2008 and application number 0950272-5 filed in Sweden on Apr. 24, 2009.

FIELD OF THE INVENTION

The present invention relates to assays for the determination of analyte concentrations which comprise the detection of binding to a ligand-supporting sensor surface, and more particularly to such assays where multiple samples are sequentially analyzed with the same ligand-supporting sensor surface with regeneration of the sensor surface between each analysis cycle.

BACKGROUND OF THE INVENTION

Analytical sensor systems that can monitor molecular interactions in real time are gaining increasing interest. These systems are often based on optical biosensors and usually referred to as interaction analysis sensors or biospecific interaction analysis sensors. A representative such biosensor system is the BIACORE™ instrumentation sold by GE Healthcare Biosciences AB (Uppsala, Sweden) which uses surface plasmon resonance (SPR) for detecting interactions between molecules in a sample and molecular structures immobilized on a sensing surface. With the BIACORE™ systems it is possible to determine in real time without the use of labeling not only the presence and concentration of a particular molecule in a sample, but also additional interaction parameters such as, for instance, the association rate and dissociation rate constants for the molecular interaction.

Generally, in a biosensor assay, when an analyte or an analyte-binding ligand, depending on the assay format, has bound to immobilized ligands on a sensor surface, the bound species are released by treatment with a suitable fluid to prepare the surface for contact with a new sample, a process referred to as regeneration. Usually, a sensor surface can be subjected to a fairly large number of analysis cycles. Many ligands (such as e.g. virus antigens), however, often have poor stability making the analyte binding capacity of the surface decrease with the number of cycles and may hamper the use of the ligand for quantitative purposes. While minor decreases in binding capacity can often be compensated by frequent calibrations, this significantly decreases the throughput and also increases the costs due to reagent consumption.

It is an object of the present invention to provide a solution to this problem and provide an assay method which minimizes the need of frequent calibrations during drift of the binding capacity of the surface and significantly improves the quality of quantitative measurements.

SUMMARY OF THE INVENTION

The above-mentioned object as well as other objects and advantages are obtained with a method which includes a normalization step wherein each analysis cycle is evaluated using a specific virtual calibration curve, i.e. each analysis cycle obtains a unique calibration curve, or specific calibration coefficients. Thereby, the number of necessary calibration runs can be minimized even in the case of a ligand-supporting sensor surfaces whose binding capacity exhibits a significant drift with the number of samples that have been analyzed with the sensor surface.

In one aspect, the present invention therefore provides a method of determining the concentration of at least one analyte in a plurality of samples by sequentially subjecting each sample to an analysis cycle comprising contacting the sample or a sample-derived solution with a sensor surface supporting a species capable of specifically binding the analyte or an analyte-binding species. The amount of binding to the sensor surface is detected, and the sensor surface is then regenerated to prepare it for the next analysis cycle. Based on the detected binding to the sensor surface the concentration of analyte in each sample is determined using virtual calibration data calculated for each analytical cycle from real calibration data obtained by contacting the sensor surface with samples containing known concentrations of analyte.

The real calibration data are obtained by calibration cycles performed at least two, preferably at three or more different times during the analysis sequence, for example initially, in the middle and at the end of the sequence of the plurality of samples. Each calibration is performed with at least two, but preferably five or more different concentrations (cycles).

In one embodiment, the virtual calibration data comprise a specific virtual calibration curve for each cycle. Such specific calibration curves may be calculated from virtual concentrations predicted for each cycle from the real calibration data, preferably by fitting each of the known concentrations of the real calibration data or curves to a model equation for the sensor response, typically using cycle number as $\underline{x}$ and response as $\underline{y}$.

In another embodiment, the virtual calibration data comprise calibration coefficients for each cycle. Such calibration coefficients may be predicted from calibration equations calculated from the real calibration data.

The ligand immobilized to the sensor surface may be an analyte-specific ligand, the analyte or an analyte analogue, or a capture agent which in turn binds an analyte-specific ligand. Various assay formats may be used, including direct assays, inhibition type assays, competition type assays and sandwich assays.

A more complete understanding of the present invention, as well as further features and advantages thereof, will be obtained by reference to the following detailed description and drawings.

DETAILED DESCRIPTION OF THE INVENTION

In brief, the present invention relates to a method for the determination of analyte concentration in multiple samples using sensor technology, typically biosensor technology, where data from calibration runs are used to calculate virtual calibration data for each analysis cycle (i.e. each sample) whereby frequent calibrations are avoided and the measurement quality is improved even when there is a substantial decrease of the binding capacity of the sensor surface with the number of analysis cycles performed.

First, with regard to biosensor technology, a biosensor is broadly defined as a device that uses a component for molecular recognition (for example a layer with immobilised antibodies) in either direct conjunction with a solid state physicochemical transducer, or with a mobile carrier bead/particle being in conjunction with the transducer. While such sensors are typically based on label-free techniques detecting a change in mass, refractive index or thickness for the immobilized layer, there are also biosensors relying on some kind of labelling. Typical sensors for the purposes of the present invention include, but are not limited to, mass detection methods, such as optical methods and piezoelectric or acoustic wave methods, including e.g. surface acoustic wave (SAW) and quartz crystal microbalance (QCM) methods. Representative optical detection methods include those that detect mass surface concentration, such as reflection-optical methods, including both external and internal reflection methods, which may be angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) (which may include scatter enhancing labels), optical wave guide sensors, external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaking mode spectroscopy, reflective interference spectroscopy (RIfS), transmission interferometry, holographic spectroscopy, and atomic force microscopy (AFR).

Biosensor systems based on SPR as well as on other detection techniques including QCM, for example, are commercially available, both as flow-through systems having one or more flow cells and as cuvette-based systems. Exemplary SPR-biosensors with multiple sensing surfaces and a flow system include the BIACORE™ systems (GE Healthcare, Uppsala, Sweden) and the PROTEON™ XPR36 system (Bio-Rad Laboratories). These systems permit monitoring of surface binding interactions in real time between a bound ligand and an analyte of interest. In this context, "ligand" is a molecule that has a known or unknown affinity for a given analyte and includes any capturing or catching agent immobilized on the surface, whereas "analyte" includes any specific binding partner thereto.

With regard to SPR biosensors, the phenomenon of SPR is well known. Suffice it to say that SPR arises when light is reflected under certain conditions at the interface between two media of different refractive indices, and the interface is coated by a metal film, typically silver or gold. In the BIACORE™ system, the media are the sample and the glass of a sensor chip which is contacted with the sample by a microfluidic flow system. The metal film is a thin layer of gold on the chip surface. SPR causes a reduction in the intensity of the reflected light at a specific angle of reflection. This angle of minimum reflected light intensity varies with the refractive index close to the surface on the side opposite from the reflected light, in the BIACORE™ system the sample side. The output from the system is a "sensorgram" which is a plot of detector response as a function of time.

A detailed discussion of the technical aspects of the BIACORE™ instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the BIACORE™ instrument may be found in U.S. Pat. No. 5,492,840. The full disclosures of the above-mentioned U.S. patents are incorporated by reference herein.

While in the Examples that follow, the present invention is illustrated in the context of SPR spectroscopy, and more particularly a BIACORE™ system, it is to be understood that the present invention is not limited to this detection method. Rather, any affinity-based detection method where a binding species, such as an analyte, binds to a ligand immobilised on a sensing surface may be employed, provided that a change at the sensing surface can be measured which is quantitatively indicative of binding of the analyte to the immobilised ligand thereon.

The method of the invention may advantageously be used with respect to any ligand which exhibits significant instability causing drift on sensor surfaces. Exemplary such ligands include virus antigens, such as hemagglutinins (HA), and the method may therefore have particular relevancy in the context of virus detection.

In the following, and for the purpose of illustration only and without any limitation thereto, the present invention will be described in more detail with respect to an assay for the detection and quantification of virus antigens, specifically an inhibition type assay for the determination of the concentration of at least one influenza virus in a sample, and more particularly of the concentrations of hemagglutinin (HA) of three different virus types in a trivalent flu vaccine.

Generally, in an inhibition type assay (also called solution competition), a known amount of a detecting molecule (here an antibody) is mixed with the sample (here a virus), and the amount of free detecting molecule in the mixture is measured. More specifically, an inhibition type assay for concentration measurements in the present biosensor context may typically comprise the following steps:

1. The ligand is attached to the sensor surface.
2. A constant concentration (which may be known or unknown) of detecting molecule is added to different concentrations of the calibrant solutions (analyte).
3. The mixtures are contacted with the sensor surface (injected over the surface in a flow system) and the response is measured.
4. Calibration curves are calculated.
5. The measurements are then performed by mixing the samples (analyte) with the constant concentration of detecting molecule, the samples are contacted with the sensor surface (injected over the surface in a flow system) and the response is measured.
6. The calibration curve is used for calculation of the analyte concentration in the sample. The amount of free detecting molecule is inversely related to the concentration of analyte in the sample.
7. The surface is regenerated and a new sample can be injected.

In the method to be described, the ligand is a virus antigen, preferably a surface antigen (or optionally the whole virus), whereas the analyte is a mixture of the antigen (virus particle, part of a virus particle or vaccine) and the detecting molecule which typically is an antibody to the antigen. The antibody may be polyclonal, e.g. serum, or monoclonal. An advantage of using the inhibition type assay format in this particular case is that diffusion effects of the large virus particles (antigen) to the surface are avoided. When the assay is (typically) used for purification of vaccine from cultured virus, the antigen may be from any part of the purification process and comprise whole virus or the final vaccine which may consist of only surface antigens.

Reference is now made to FIGS. 1 to 12 in the accompanying drawings. As schematically depicted in FIG. 1*a*, purified virus HA designated by reference numeral 1 is immobilized on a biosensor sensor surface 2. A mixture of virus particles 3 and anti-serum containing antibodies 4 is made to pass as a liquid flow over the sensor surface 2. As illustrated in FIG. 1*a*, the antibodies 4 can either be bound to the virus particle or to the immobilized HA antigen or be free in solution. Binding to the sensor surface increases the response signal from the sensor surface.

FIG. 1*b* illustrates the case when no virus is present in the sample. A maximum amount of antibodies 4 then bind to the HA antigen 1 on the sensor surface, resulting in a high response signal.

In FIG. 1*c*, on the other hand, a high concentration of virus particles 3 results in a low amount of free antibodies 4, and a low response signal is therefore measured. Thus, the higher the concentration of virus is in the sample, the lower is the amount of binding antibodies to the surface HA, resulting in a lower response level.

If the sensor surface has, or is capable of providing multiple discrete sensing areas or "spots", such as three or more, e.g. three different HA' s may be immobilized as is schematically illustrated in FIG. 2, where HA specific to virus types/subtypes A/H1N1, A/H3N2 and B (which are typically used in current flu vaccines) are immobilized to the respective spots on the sensor surface.

As will be demonstrated below, the binding of different virus anti-sera to HA is selective, i.e. there is no cross-reactivity between different virus types or subtypes. Due to this selectivity, two or more different virus components in a sample, such as a multivalent vaccine, may be determined simultaneously.

An exemplary method embodiment of the invention applied to a sample containing the three above-mentioned virus types/subtypes A/H1N1, A/H3N2 and B will now be described.

HA from the three different virus types is immobilized on three different spots on the sensor surface.

A calibration procedure is then performed. Calibrants consisting of a fixed concentration of a standard anti-serum for each virus type are mixed with different known concentrations of virus (or virus antigen) covering the concentration range to be measured. The calibrants are then injected, either separately or together for all three types, over the sensor surface spots and the response is measured. From the results of the measurements, calibration curves are then calculated.

For illustration, FIG. 12 shows an example of sensorgrams (detector response vs time curves) obtained with a BIACORE™ system for a number of virus standards which together will provide a typical calibration curve.

Measurement of the sample content of virus HA is then performed by mixing each sample with the fixed concentration of the anti-serum, either one at a time, or, preferably, with all three anti-sera. The sample is injected over the sensor surface and the free anti-sera concentration is measured. The calibration curve is used for the calculation of virus antigen concentration in the sample.

The surface is then regenerated (i.e. bound antibodies are dissociated from the immobilized HA by contacting the surface with a suitable regeneration solution), and a new sample can be passed over the surface.

Since, as mentioned above, the immobilized antigen is not stable, this causes the capacity of the sensor surface to decrease. The measured/calculated concentration of the controls therefore increases as a function of the number of analysis cycles performed (or cycle number) until a new calibration run is performed, since in the inhibition type assay format the calibration curve interprets the binding capacity decrease as an increased HA concentration in the sample. This drift increases with an increased number of analysis cycles, and is usually not linear, typically exponential. An "analysis cycle", as the term is used herein, includes the steps of passing the mixture of virus and detecting antibodies over the sensor surface with immobilized HA, and then regenerating the surface to prepare it for the next analysis cycle.

Therefore, according to the present invention, based on the usually multiple calibrations performed (e.g. initially, in the middle and end of the analysis sequence), each analysis cycle is evaluated using "virtual" calibration data calculated to be specific for each analysis cycle. Thereby the need of frequent calibration during drift is effectively minimized and the quality of quantitative measurements using biosensor systems, such as e.g. the above-mentioned BIACORE™ systems is considerably improved. This new calibration routine can be designed in different ways.

In one variant, raw data from calibration runs is used for prediction of virtual concentrations for each analysis cycle followed by calculation of a cycle specific calibration curve and prediction of the concentrations for the samples and the controls.

More particularly, for each calibration performed with a suitable number of different concentrations, the responses obtained are fitted to a model function, e.g. using cycle number as $\underline{x}$ and response as $\underline{y}$. The model function or equation may, for example, be an exponential function, e.g. a double exponential function or a standard type regression curve model for ligand binding, such as the "four parameter regression curve" (below also referred to as "four parameter equation") described in the Examples below. The equations or curves produced (one for each concentration) are then used to calculate a virtual response for each analysis cycle. These virtual response data are then used to calculate a specific calibration curve for each cycle, which may be done by using, for example, the above-mentioned four parameter regression curve. These cycle specific calibration curves are then used for prediction of the concentrations of the samples and the controls.

In another variant, calibration equations are calculated for each of the real calibrations followed by prediction of specific calibration coefficients for each analysis cycle. These coefficients are then used for prediction of the concentrations of the samples and the controls.

More particularly, using the calibration data obtained at different times during the analysis cycle sequence, the coefficients of a regression curve model are calculated for each calibration. The regression curve model may, for example, be a standard type regression curve model for ligand binding, such as the above-mentioned "four parameter regression curve", in which case four coefficients are calculated. For each coefficient, its variation with cycle number is then determined, whereupon concentrations may be calculated from the regression curve model used.

Figure 11A:
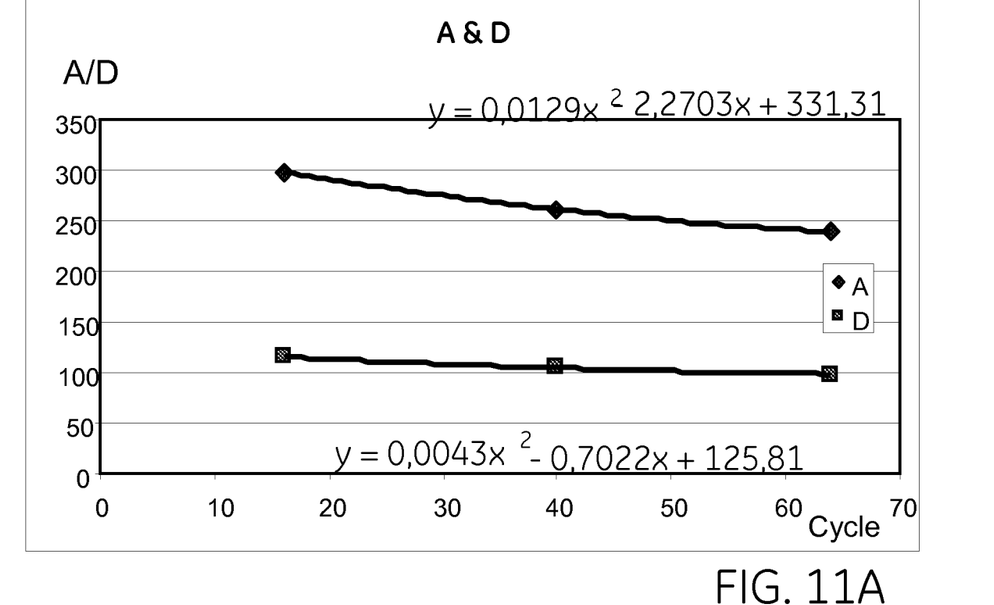
FIG. 11 shows variation of the four coefficients of a four-parameter equation with cycle number.
Figure 11B:
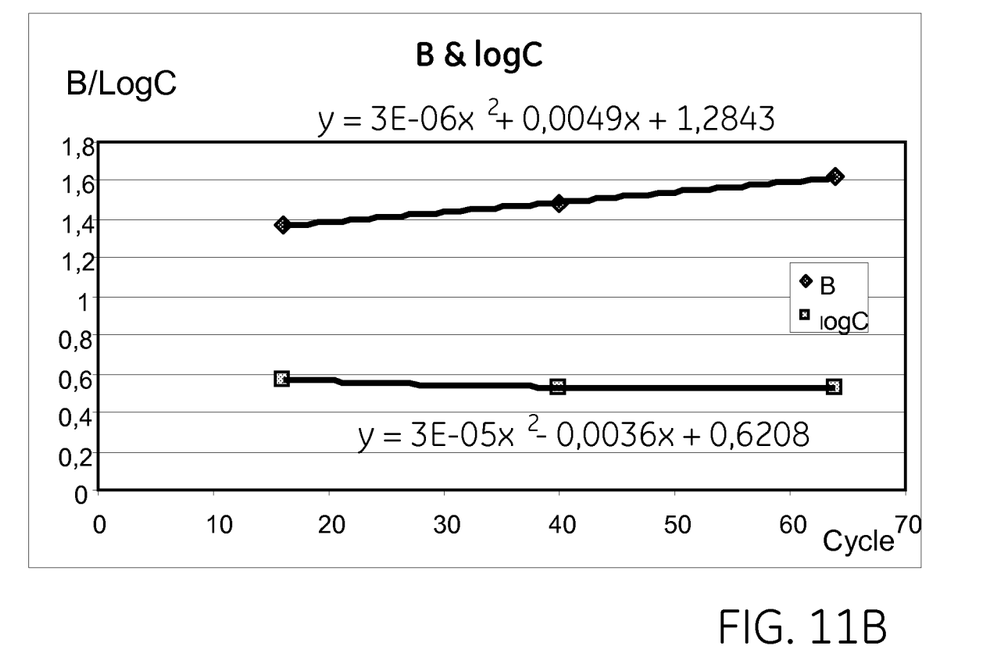
Figure 12:
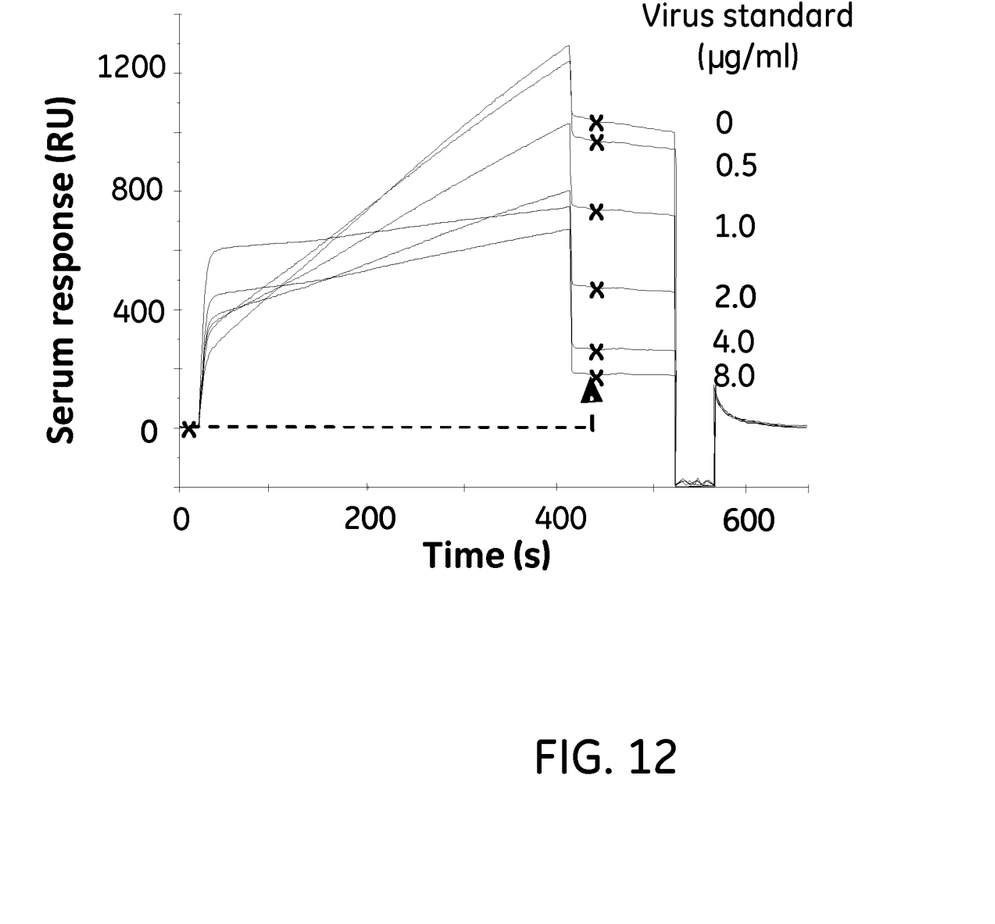
FIG. 12 shows a number of sensorgrams for virus standards forming the basis of a typical calibration curve.

An illustrative example of the variation of each one of the four coefficients (parameters) of the "four parameter regression curve" mentioned above is shown in FIGS. 11A (coefficients A=$R_{high}$, and D=$R_{low}$) and 11B (coefficients B=$A_2$ and log C=log $A_1$). The equations indicated for each curve were obtained by plotting the respective coefficients as a function of cycle number.

The necessary number of calibrations and different concentrations generally depend on the regression curve models used. While at least for rather small concentration ranges, calibrations at two different analysis cycle numbers and two different concentrations may be sufficient (linear regression curve model), it is preferred to perform at least three, e.g. three or four calibrations, and to use at least 5, typically 6 to 8 different concentrations (exponential or "four parameter regression curve").

The first-mentioned method variant, which will be described in more detail in Examples 4 and 5 below, typically comprises the following steps:

perform calibrations with different concentrations at different times during the analysis sequence to obtain a number of calibration curves;

fit calibration curves to four-parameter equation or double exponential function, for each concentration using cycle as $\underline{x}$ and detector response as $\underline{y}$ to obtain corresponding response versus cycle curves;

calculate from the different response versus cycle curves for the respective concentrations virtual responses for each cycle;

fit to four-parameter equation to calculate a specific calibration curve for each cycle; and determine the analyte concentration in each sample from the respective cycle specific calibration curve.

The second method variant, which will be described in more detail in Example 6, typically comprises the following steps:

perform calibrations with different concentrations at different times during the analysis sequence to obtain a number of calibration curves;

fit the calibration curves to the "four-parameter equation" to determine values for the four coefficients for each calibration curve;

plot coefficient values against cycle number for all concentrations to obtain virtual coefficients for each cycle; and calculate the analyte concentration in each sample from the four-parameter equation using the cycle specific coefficients.

In the following Examples, various aspects of the present invention are disclosed more specifically for purposes of illustration and not limitation.

EXAMPLES

The present examples are provided for illustrative purposes only, and should not be construed as limiting the invention as defined in the appended claims.

Instrumentation

A BIACORE™ T100 (GE Healthcare, Uppsala, Sweden) was used. This instrument, which is based on surface plasmon resonance (SPR) detection at a gold surface on a sensor chip, uses a micro-fluidic system (integrated micro-fluidic cartridge—IFC) for passing samples and running buffer through four individually detected flow cells, designated Fc 1 to Fc 4, one by one or in series. The IFC is pressed into contact with the sensor chip by a docking mechanism within the BIACORE™ T100 instrument.

A sensor chip was used Sensor Chip CM5 (GE Healthcare, Uppsala, Sweden) which has a gold-coated (about 50 nm) surface with a covalently linked hydrogel matrix (about 100 nm) of carboxymethyl-modified dextran polymer.

The output from the instrument is a "sensorgram" which is a plot of detector response (measured in "resonance units", RU) as a function of time. An increase of 1000 RU corresponds to an increase of mass on the sensor surface of approximately 1 ng/mm$^2$.

Example 1

Assay for Influenza Virus A/H3N2/Wyoming, A/H3N2/New York and B/Jilin

Materials
Hemagglutinin (HA) A/H3N2, Wyoming/3/2003, Wisconsin and New York was from Protein Sciences Corp., Meriden, USA.
HA A/H1N1, New Caledonia/20/99 was from ProsPec, Rehovot, Israel.
HB/Jilin was from GenWay Biotech Inc., San Diego, USA.

Sera as well as virus strains were from NIBSC—National Institute for Biological Standards and Control, Potters Bar, Hertfordshire, U.K.
Assay and sample buffer: HBS-EP+, GE Healthcare.
Surfactant P20, GE Healthcare.
Method
HA (H3N2, H1N1 and B) are immobilized to a Sensor Chip CM5 in three respective flow cells of the BIACORE™ T100 using amine coupling as follows:
H3N2/Wyoming and Wisconsin: 10 µg/ml in 10 mM phosphate buffer, pH 7.0, 0.05% Surfactant P20, 7 min.
H3N2/New York: 10 µg/ml in 10 mM maleate buffer, pH 6.5, 0.05% Surfactant P20, 7 min.
B/Jilin: 5 µg/ml in 10 mM maleate buffer, pH 6.5, 0.05% Surfactant P20, 20-30 min.
Immobilisation levels are 5000-10000 RU.
Sera to the respective virus strains are diluted to obtain approximately 500-1500 RU.
3-10 start-up cycles with serum are performed.
Calibration curves are prepared with virus antigen (HA), first diluted in MQ as recommended by the supplier (HA is then kept frozen in aliquots) and then further diluted in sera to typically 0.1-15 µg/ml.
Standards and samples have 400 s injection time.
Regeneration is performed with 50 mM HCl, 0.05% Surfactant P20, 30 s followed by 30 s stabilization.

Example 2

Generality of Detection of Different Strains of the Same Virus Subtype

Figure 1:
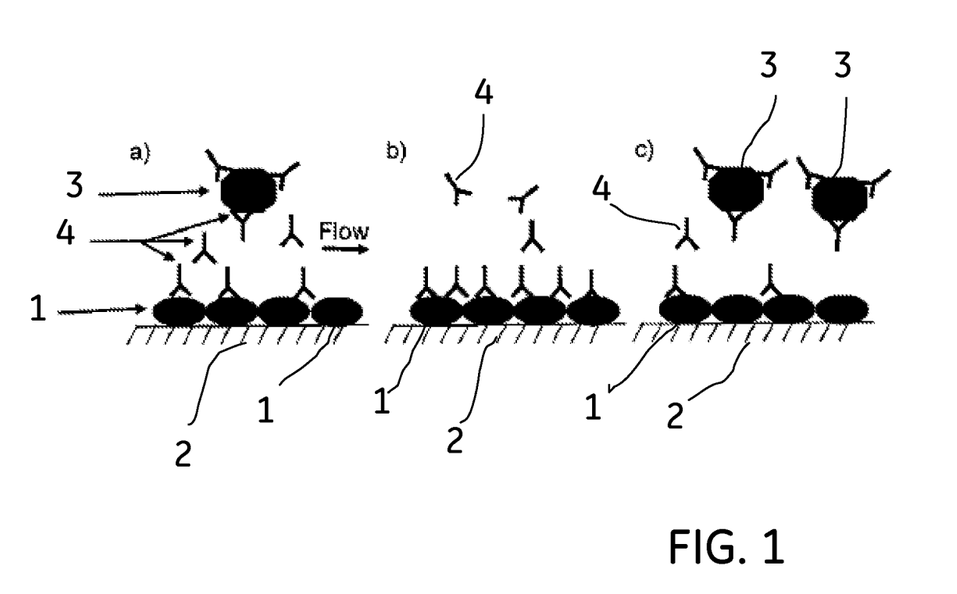
FIG. 1 is a schematic illustration of an inhibition type virus assay on a sensor surface for three cases (a-c) with different virus concentrations in the sample.
Figure 2:
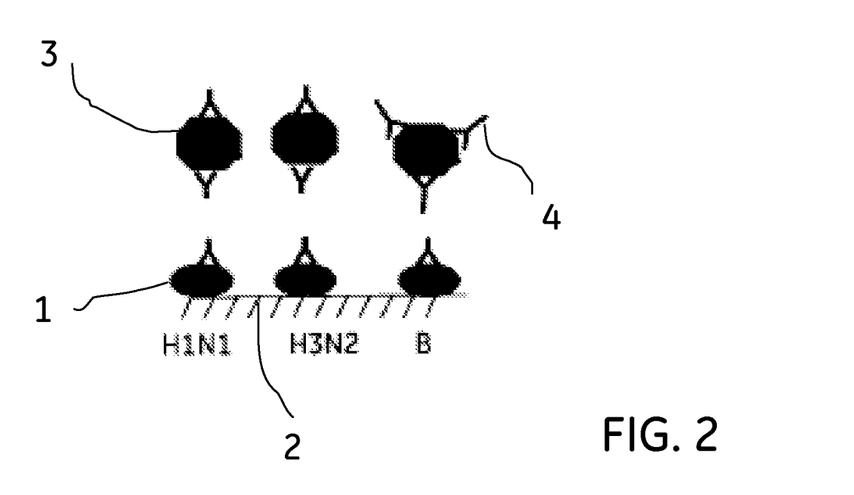
FIG. 2 is a schematic illustration similar to FIG. 1 where three different virus antigens are immobilized to respective separate spots on a sensor surface and three different antibodies specific for each antigen are used for quantification.
Figure 3:
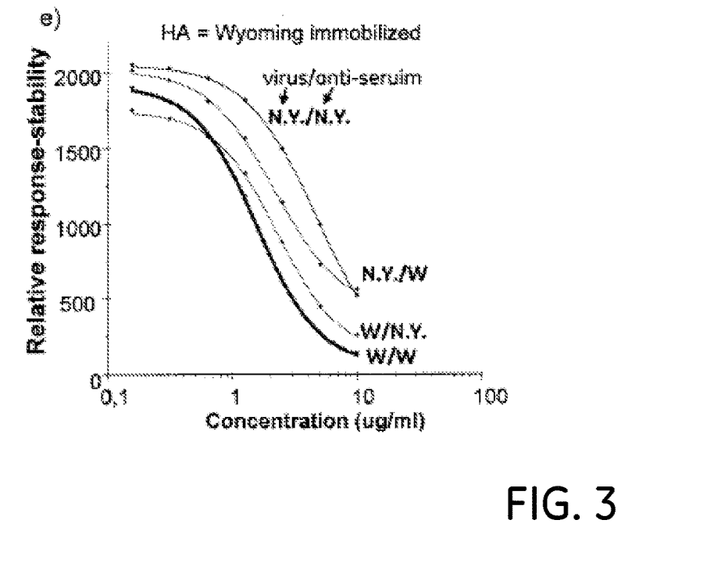
FIG. 3 is a diagram showing measured relative response/stability versus concentration of different influenza virus/anti-serum mixtures in an inhibition type assay with immobilized influenza virus antigen on a sensor surface.

H3N2 strain Wyoming HA was immobilized to a Sensor Chip CM5 and the surface was contacted with different virus/antiserum combinations: virus/anti-serum from Wyoming (W/W); virus/anti-serum from New York (N.Y./N.Y.), Wyoming virus and serum from New York (W/N.Y.); New York virus and serum from Wyoming (N.Y./W). Calibration curves with the respective combinations were run. The results are shown in FIG. 3. From the figure, it is clear that there is cross-reactivity between the different virus strains. The Wyoming HA and virus/anti-serum can therefore be used for quantification of the New York strain and vice versa.

Example 3

Figure 4:
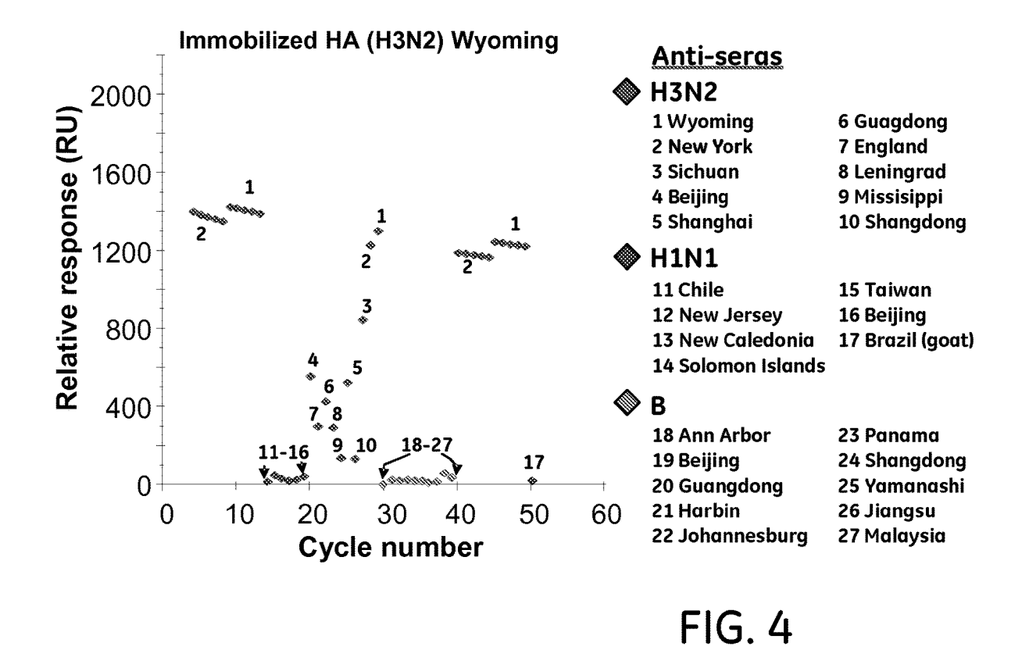
FIG. 4 is a diagram showing measured relative response versus analysis cycle number for the binding of a plurality of different influenza virus anti-sera to a sensor surface with immobilized influenza virus antigen.

Selectivity in Binding of Anti-Sera to Different Influenza Virus Types/Subtypes HA 27 different anti-sera to different strains of influenza virus A/H3N2, A H1N1 and B were injected over immobilized H3N2 Wyoming HA and the binding thereof was detected. The results as well as a listing of the strains used are indicated in FIG. 4. As apparent from the figure, all H3N2 anti-sera bind with signals higher than 100 RU while all H1N1 and B anti-sera have signals below 50 RU. This indicates that several virus strains may be quantified simultaneously and that one or only a few HA's are required for measurement of H3N2.

Example 4

Virtual Calibration Procedure

Figure 5:
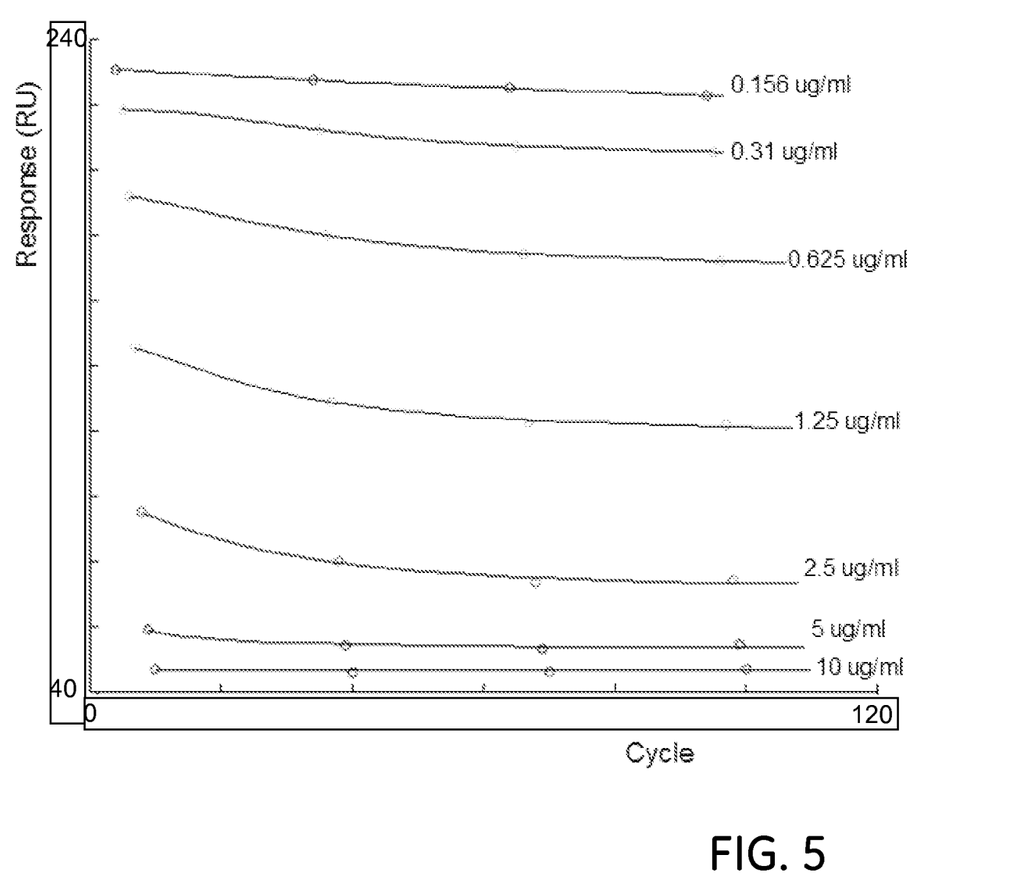
FIG. 5 is a diagram showing fitted normalisation curves based on cycle number as x and the measured response as y for seven concentrations (0.156, 0.31, 0.625, 1.25, 2.5, 5 and 10 μg/ml) of virus control samples at four ordinary calibrations in an inhibition type assay run on a sensor surface with immobilized virus antigen. These normalisation curves are used for prediction of virtual concentrations for each cycle. These virtual concentrations are then used for the construction of a cycle specific calibration curve using the virtual concentration as x and the known concentration as y.

A number of assay cycles (about 100) were run on the BIACORE™ T100 and a Sensor Chip CM5, during which four ordinary calibrations were performed with seven different concentrations of control samples (0.156, 0.31, 0.625, 1.25, 2.5, 5 and 10 µg/ml). The function $y(x)=a*\exp(-b*x)+c*\exp(-d*x)+e$, using cycle number as $x$, response as $y$, and a, b, c, d and e as fitted parameters, was fitted for each of the seven different concentrations. The results are shown in FIG. 5, where the top curve represents the lowest concentration (0.156 µg/ml) of the control (i.e. the highest response—inhibition assay) and the bottom curve the highest (10 µg/ml) (i.e. the lowest response). The equations were then used for calculation of a virtual response for each cycle. These responses were then used for the calculation of a calibration curve for each cycle, using the standard type "four parameter regression curve" described in Example 6 below. From these cycle specific calibration curves, predictions of samples and controls run at exactly that cycle were made, as described below with reference to FIGS. 6 and 7.

Figure 6:
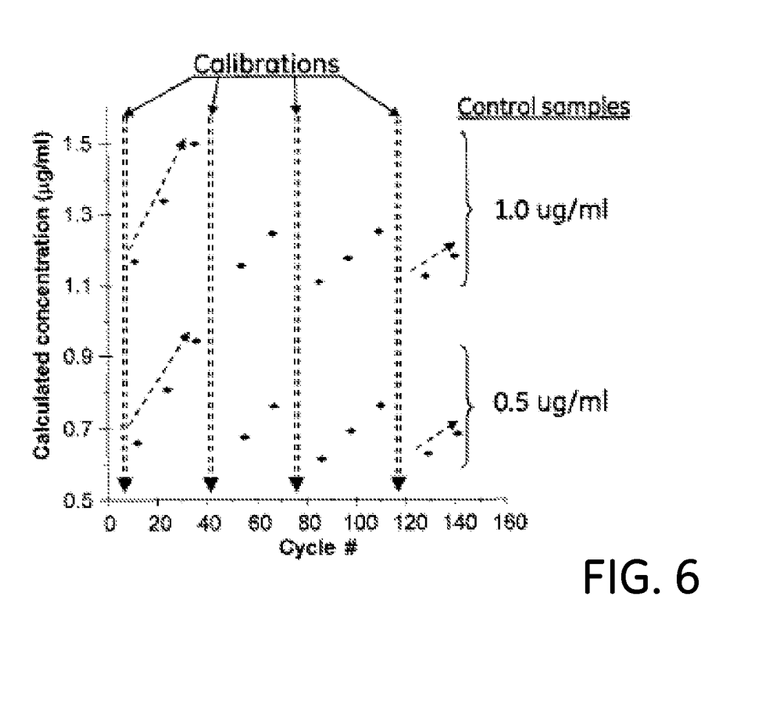
FIG. 6 is a diagram showing calculated concentration versus analysis cycle number for two different control sample concentrations with four ordinary calibrations at different cycle numbers in an inhibition type assay run on a sensor surface with immobilized virus antigen.

FIG. 6 illustrates the drift on the calculated concentration of 2 controls, 1.0 µg/ml and 0.5 µg/ml. A large number of assay cycles were run and four intermediate calibrations were performed at cycle numbers indicated by the double dotted arrows. The concentrations of the 3 (2) controls following each calibration were calculated against the closest preceding calibration curve. As indicated by the dotted arrows, there is a systematic increase in calculated concentrations with increased distance to the calibration. This increase in calculated concentration is due to a decreased signal from the control sample. This is in turn due to a decrease in binding capacity of the surface as a function of cycle numbers, which the calibration curve interprets as an increased concentration. This decrease in binding capacity is also visible in FIG. 3 and FIG. 4.

Figure 7:
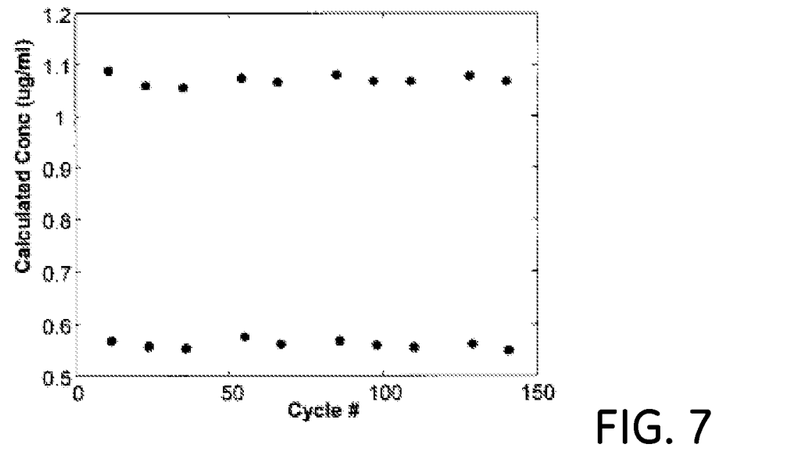
FIG. 7 is a diagram showing application of a virtual calibration curve (according to FIG. 5) for each cycle to the same raw data as in FIG. 6 for two control sample concentrations.

Application of the virtual calibration method described above to the raw data in FIG. 6 gives the concentration estimates for shown in FIG. 7 for the 0.5 and 1.0 µg/ml controls, which is a considerable improvement of the repeatability in the prediction of the concentration of control samples.

Example 5

Normalization of Binding Data by a Virtual Calibration Procedure

Figure 8:
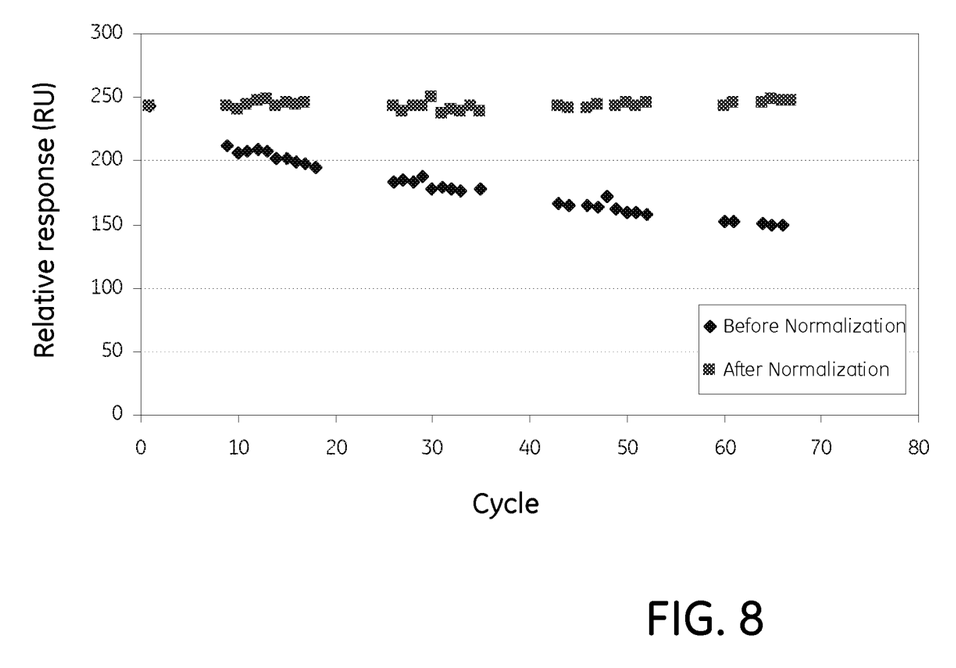
FIG. 8 is a similar diagram as FIG. 7 showing measured binding data for a control sample and corresponding data normalized by a virtual calibration curve for each cycle.

HA recombinant proteins HB/Jilin, H1N1/New Caledonia and H3N2/Wyoming were immobilized. Calibration curves were obtained. Samples were diluted and concentrations between 0.5-15 µg/ml were measured and recalculated. To avoid drift of the response, the results were normalized using the normalization procedure outlined in Example 4 above, each cycle obtaining a unique calibration curve. FIG. 8 shows the results before and after normalization for control samples, 5 µg/ml of B/Jiangsu/10/2003, giving a response of 250 RU, CV=1.2%.

Example 6

Simultaneous Detection of Three Different Virus Types

Three flow cells were immobilized with three different recombinant influenza virus HA proteins: H1N1/New Caledonia, H3N2/Wisconsin and Bailin.

Virus standards from the three influenza strains, H1N1/New Caledonia, H3N2/Wisconsin and B/Malaysia, were diluted and mixed together so that the final concentration of each standard was 16 µg/ml. Calibration curves were then made as 2-fold serial dilutions from 16 µg/ml to 0.5 µg/ml.

The three vaccines, H1N1, H3N2 and B, to be analysed, were diluted 8, 16, 32 and 64 times.

Three serums (H1N1/New Caledonia, H3N2/Wisconsin and B/Malaysia from NIBSC) were diluted to concentrations giving responses of 500-700 RU, and mixed together.

To analyze the vaccines, duplicates of the standards and vaccines were first mixed with the serum solution and then allowed to flow through all flow cells using a method created in "Method Builder".

The general method from "Method Builder":
Start-up (7 cycles, serum only, followed by regeneration)
Calibration curve 1 (14 cycles)
Samples (12 cycles)
Calibration curve 2 (14 cycles)
Samples (12 cycles)
Calibration curve 3 (14 cycles).

Figure 9A:
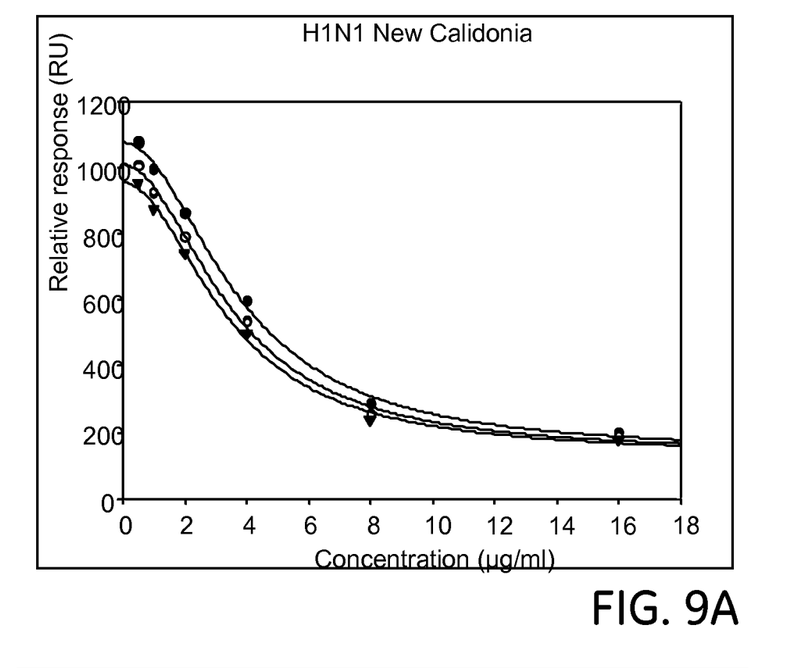
FIGS. 9A-C show calibration curves prepared in an assay for simultaneous detection of three different virus types.
Figure 9B:
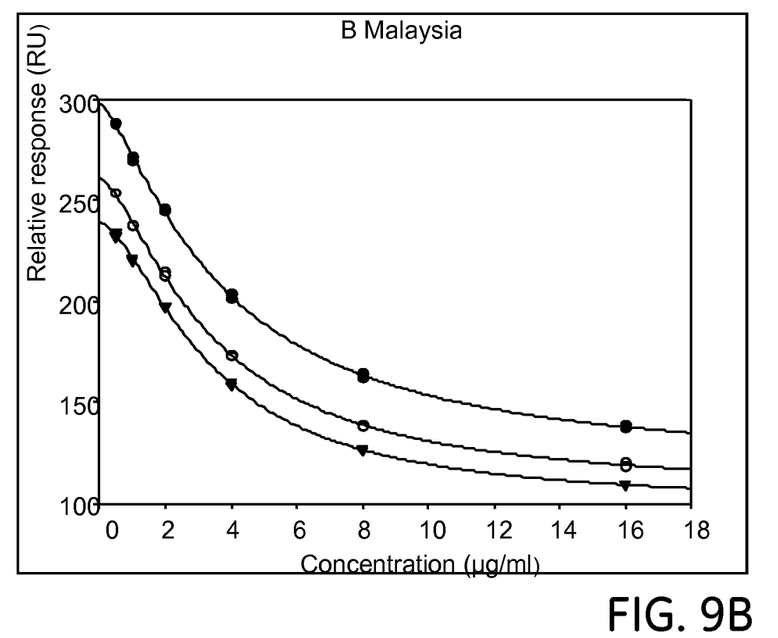
Figure 9C:
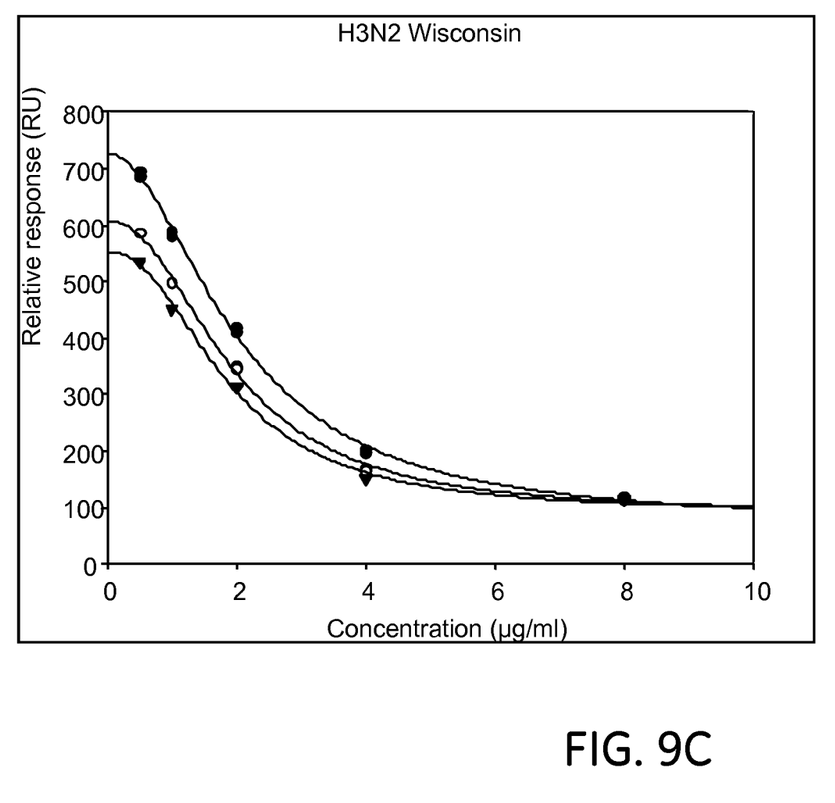

The calibration curves 1-3 for each strain are shown in FIGS. 9A-C, where in each figure calibration curve 1 is the top curve, calibration curve 2 is the middle curve and calibration curve 3 is the bottom curve.

The results were then normalized in respect to the three calibration curves. This was done by performing a four parameter fit of the calibration curves to the four-parameter regression curve (Equation 1) conventionally used for concentration determinations with BIACORE™ systems to determine the four coefficients:

$$\text{Response} = R_{high} - \frac{(R_{high} - R_{low})}{1 + \left(\frac{X}{A_1}\right)^{A_2}} \quad (1)$$

where $R_{high}$ is the response at low virus concentration, $R_{low}$ is the response at low virus concentration, $A_1$ (EC50) and $A_2$ (Hill slope) are fitting parameters and X is the concentration of virus.

The values obtained for each one of the four coefficients at the different concentrations were then plotted against analysis cycle number, whereby an equation for each coefficient was obtained. Using the coefficients obtained with Equation 1 above, the normalized concentrations were calculated.

Results

| Surface HA | Sample | Concentration (µg/ml) | Std dev | CV % |
|---|---|---|---|---|
| B | vaccine 1 | 102.9 | 1.07 | 1.0 |
|  | vaccine 2 | 30.9 | 0.30 | 1.0 |
|  | vaccine 3 | 27.8 | 0.44 | 1.6 |
| H1N1 | vaccine 1 | 37.4 | 0.05 | 0.1 |
|  | vaccine 2 | 34.9 | 0.04 | 0.1 |
|  | vaccine 3 | 30.5 | 0.10 | 0.3 |
| H3N2 | vaccine 1 | 36.2 | 0.02 | 0.1 |
|  | vaccine 2 | 27.8 | 0.06 | 0.2 |
|  | vaccine 3 | 37.7 | 0.12 | 0.3 |

According to the manufacturers, the HA concentration of each strain in the vaccine should be 30 µg/ml, analyzed with SRID.

Example 7

Determination of CHO-HCP

Figure 10:
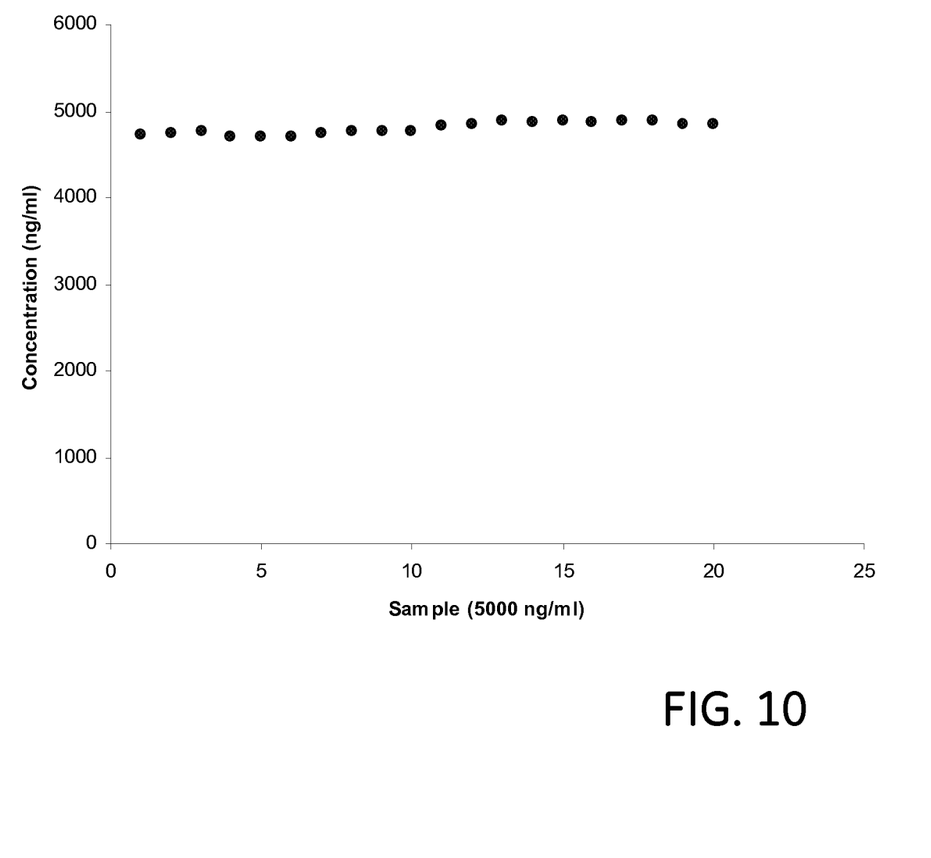
FIG. 10 shows plotted analyte concentrations evaluated with virtual calibration.

A method was set for the BIACORE™ T100 instrument to determine concentrations of twenty samples of CHO-HCP (Chinese hamster ovary host cell protein) with a concentration of 5000 ng/ml. Three standard curves were run, in the beginning, in the middle and in the end, using 6-8 concentrations for each standard curve. The twenty samples were injected for 300 s over a sensor chip surface immobilized with anti-CHO HCP. Regeneration was performed with 10 mM Glycine-HCl, pH 1.5 for 60 s. Evaluation of the concentrations was performed by virtual calibration, and for comparison using an average curve and closest preceding calibration curve, respectively. The results are shown in the tables below and in FIG. 10. As can be seen therein, the concentrations evaluated with virtual calibration had an average concentration of 4798 ng/ml with a CV (%) of 1.45. Evaluating concentrations using an average curve gave an average concentration of 4795 ng/ml with a CV (%) of 9.87. Using the preceding calibration curve for evaluation of the samples gave an average concentration of 4408 with a CV (%) of 4.76.

Virtual Calibration

| Sample | Conc. | Response (RU) | Cal. Conc. (ng/ml) | CV (%) |
|---|---|---|---|---|
| 1 | 5000 ng/ml | 223.2 | 4718 | |
| 2 | 5000 ng/ml | 222.1 | 4733 | |
| 3 | 5000 ng/ml | 221.3 | 4762 | |
| 4 | 5000 ng/ml | 218.8 | 4702 | |
| 5 | 5000 ng/ml | 217.4 | 4694 | |
| 6 | 5000 ng/ml | 216.2 | 4696 | |
| 7 | 5000 ng/ml | 215.9 | 4744 | |
| 8 | 5000 ng/ml | 214.9 | 4759 | |
| 9 | 5000 ng/ml | 214 | 4772 | |
| 10 | 5000 ng/ml | 212.9 | 4771 | |
| 11 | 5000 ng/ml | 205.2 | 4820 | |
| 12 | 5000 ng/ml | 204.8 | 4845 | |
| 13 | 5000 ng/ml | 204.7 | 4880 | |
| 14 | 5000 ng/ml | 203.6 | 4860 | |
| 15 | 5000 ng/ml | 203.2 | 4877 | |
| 16 | 5000 ng/ml | 202.5 | 4870 | |
| 17 | 5000 ng/ml | 202.1 | 4884 | |
| 18 | 5000 ng/ml | 201.4 | 4883 | |
| 19 | 5000 ng/ml | 200.3 | 4846 | |
| 20 | 5000 ng/ml | 199.7 | 4842 | |
| Avg. | | | 4798 | 1.447 |

Concentration Analysis (Calculated with an Average Curve)

| Sample | Conc. | Response (RU) | Calc. Conc. (ng/ml) | CV (%) |
|---|---|---|---|---|
| 1 | 5000 ng/ml | 223.2 | 5573 | |
| 2 | 5000 ng/ml | 222.1 | 5502 | |
| 3 | 5000 ng/ml | 221.3 | 5449 | |
| 4 | 5000 ng/ml | 218.8 | 5295 | |
| 5 | 5000 ng/ml | 217.4 | 5206 | |
| 6 | 5000 ng/ml | 216.2 | 5132 | |
| 7 | 5000 ng/ml | 215.9 | 5112 | |
| 8 | 5000 ng/ml | 214.9 | 5057 | |
| 9 | 5000 ng/ml | 214 | 5002 | |
| 10 | 5000 ng/ml | 212.9 | 4934 | |
| 11 | 5000 ng/ml | 205.2 | 4495 | |
| 12 | 5000 ng/ml | 204.8 | 4475 | |
| 13 | 5000 ng/ml | 204.7 | 4466 | |
| 14 | 5000 ng/ml | 203.6 | 4409 | |
| 15 | 5000 ng/ml | 203.2 | 4387 | |
| 16 | 5000 ng/ml | 2025 | 4346 | |
| 17 | 5000 ng/ml | 202.1 | 4325 | |
| 18 | 5000 ng/ml | 201.4 | 4293 | |
| 19 | 5000 ng/ml | 200.3 | 4232 | |
| 20 | 5000 ng/ml | 199.7 | 4201 | |
| Avg. | | | 4795 | 9.87 |

Concentration analysis (Calculated with the Closest Curve)

| Sample | Conc. | Response (RU) | Calc. Conc. (ng/ml) | CV (%) | Calib. Curve |
|---|---|---|---|---|---|
| 1 | 5000 ng/ml | 223.2 | 4529 | | 1 |
| 2 | 5000 ng/ml | 222.1 | 4473 | | 1 |
| 3 | 5000 ng/ml | 221.3 | 4432 | | 1 |
| 4 | 5000 ng/ml | 218.8 | 4311 | | 1 |
| 5 | 5000 ng/ml | 217.4 | 4240 | | 1 |
| 6 | 5000 ng/ml | 216.2 | 4181 | | 1 |
| 7 | 5000 ng/ml | 215.9 | 4166 | | 1 |
| 8 | 5000 ng/ml | 214.9 | 4122 | | 1 |
| 9 | 5000 ng/ml | 214 | 4079 | | 1 |
| 10 | 5000 ng/ml | 212.9 | 4025 | | 1 |
| 11 | 5000 ng/ml | 205.2 | 4698 | | 2 |
| 12 | 5000 ng/ml | 204.8 | 4677 | | 2 |
| 13 | 5000 ng/ml | 204.7 | 4667 | | 2 |
| 14 | 5000 ng/ml | 203.6 | 4607 | | 2 |
| 15 | 5000 ng/ml | 203.2 | 4585 | | 2 |
| 16 | 5000 ng/ml | 202.5 | 4542 | | 2 |
| 17 | 5000 ng/ml | 202.1 | 4520 | | 2 |
| 18 | 5000 ng/ml | 201.4 | 4486 | | 2 |
| 19 | 5000 ng/ml | 200.3 | 4422 | | 2 |
| 20 | 5000 ng/ml | 199.7 | 4390 | | 2 |
| Avg. | | | 4408 | 4.758 | |

From the foregoing, it will be appreciated that, although specific embodiments of this invention have been described herein for purposes of illustration, various modifications may be made without departing from the spirit and scope of invention. Accordingly, the invention is not limited except by the appended claims.

What is claimed is:

1. A method for determining concentration of a target analyte by determining binding of the target analyte to a sensor surface of an analytical sensor system by an analysis sequence, the method comprising:
sequentially subjecting each target sample of a plurality of target samples comprising at least one target analyte to a sample analysis cycle, resulting in a plurality of sample analysis cycles with one sample analysis cycle corresponding to one target sample, wherein each sample analysis cycle comprises:
detecting an amount of target analyte binding to the sensor surface from contact between one of the plurality of target samples and the sensor surface of a sensor, the sensor surface supporting a species capable of specifically binding the target analyte; and
regenerating the sensor surface;
running two or more calibration cycles at different times during the analysis sequence to obtain real calibration data, wherein each calibration cycle comprises sequentially subjecting each calibration sample of a plurality of calibration samples comprising different known concentrations of a control analyte to a calibration analysis cycle to generate real calibration data for the plurality of calibration samples, wherein the calibration analysis cycle comprises:
contacting one of the plurality of calibration samples with the sensor surface supporting the species capable of specifically binding the control analyte;
detecting an amount of control analyte binding to the sensor surface to generate the real calibration data; and
regenerating the sensor surface;
calculating virtual calibration data for the target sample associated with each sample analysis cycle from the real calibration data from the calibration samples and control analyte by fitting the real calibration data to a model function for sensor response using the respective sample analysis cycle, wherein the virtual calibration data is unique to the respective sample analysis cycle for the respective target sample;
generating a virtual calibration curve for each sample analysis cycle based on the virtual calibration data calculated for each sample analysis cycle, wherein the respective sample analysis cycle forms an x axis and the sensor response forms a y axis in the virtual calibration curve, the virtual calibration curve to improve performance of the sensor for the respective sample analysis cycle;
determining the concentration of analyte in each target sample using the corresponding detected amount of target analyte binding and the corresponding virtual calibration curve in place of a real calibration curve for each sample analysis cycle;
outputting the concentration of analyte in each target sample from the sensor to adjust monitoring of molecular interaction by the analytical sensor system; and
controlling throughput of a biosensor assay using the concentration output by the analysis sequence of the analytical sensor system.

2. The method of claim 1, wherein calculating virtual calibration data comprises determining a sensor response-cycle number relationship for each calibration sample.

3. The method of claim 1, wherein the determining comprises determining a concentration of at least one influenza virus.

4. The method of claim 1, wherein the determining comprises determining a concentration of hemagglutinin (HA) of three different virus types in a trivalent flu vaccine.

5. The method of claim 1, wherein outputting the concentration of analyte further comprises outputting a sensorgram based on the detected amount of target analyte binding to the sensor surface.

6. The method of claim 1, wherein the model function is a standard type regression curve for ligand binding.

7. The method of claim 6, wherein the model function includes a four-parameter fit of calibration curves to a four-parameter regression curve.

8. The method of claim 7, wherein the four-parameter fit is determined according to $$\text{Response} = R_{high} - \frac{(R_{high} - R_{low})}{1 + \left(\frac{X}{A_1}\right)^{A_2}},$$

wherein $R_{high}$ h is the sensor response at a high virus concentration, Rim is the sensor response at a low virus concentration, $A_1$ and $A_2$ are fitting parameters, and X is a concentration of virus.

9. The method of claim 1, wherein the model function is an exponential function.

10. The method of claim 9, wherein the exponential function comprises $y(x)=a*\exp(-b*x)+c*\exp(-d*x)+e$, wherein x represents the respective sample analysis cycle, y represents the sensor response, and a, b, c, d and e represent fitted parameters fitted for a plurality of concentrations.

11. The method of claim 1, wherein the virtual calibration data comprise specific calibration coefficients for each sample analysis cycle.

12. The method of claim 11, wherein calculating virtual calibration data comprises calculating calibration equations from the real calibration data, and wherein virtual calibration coefficients for each sample analysis cycle are calculated therefrom.

13. The method of claim 12, wherein calculating virtual calibration data comprises plotting the virtual calibration coefficient values against a respective cycle number for each sample analysis cycle.

14. The method of claim 1, wherein each sample analysis cycle is based on an assay format selected from a direct assay, an inhibition assay, a competitive assay, and a sandwich assay.

15. The method of claim 14, wherein at least one sample analysis cycle is based on a direct type assay.

16. The method of claim 14, wherein at least one sample analysis cycle is based on an inhibition type assay, and wherein each of the target samples are mixed with a constant amount of a detecting molecule.

17. The method of claim 1, wherein three calibration cycles are run at different times during the analysis.

18. The method of claim 17, wherein each calibration cycle comprises sequentially subjecting five to eight calibration samples having different known concentrations of the control analyte to the calibration analysis cycle.

* * * * *